(12) United States Patent
Rabbat et al.

(10) Patent No.: US 11,127,503 B2
(45) Date of Patent: *Sep. 21, 2021

(54) SYSTEM AND METHOD FOR ASSESSING CARDIOVASCULAR DISEASE AND TREATMENT EFFECTIVENESS FROM ADIPOSE TISSUE

(71) Applicant: HeartFlow, Inc., Redwood City, CA (US)

(72) Inventors: Mark Rabbat, Redwood City, CA (US); Charles Taylor, Atherton, CA (US); Michiel Schaap, Redwood City, CA (US); Timothy Fonte, San Francisco, CA (US); Leo Grady, Darien, CT (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/218,844

(22) Filed: Mar. 31, 2021

(65) Prior Publication Data

US 2021/0217534 A1 Jul. 15, 2021

Related U.S. Application Data

(63) Continuation of application No. 16/654,698, filed on Oct. 16, 2019.
(Continued)

(51) Int. Cl.
*G16H 50/30* (2018.01)
*G16H 50/50* (2018.01)
(Continued)

(52) U.S. Cl.
CPC ......... *G16H 50/30* (2018.01); *A61B 5/02007* (2013.01); *A61B 5/4848* (2013.01);
(Continued)

(58) Field of Classification Search
CPC ....... A61B 6/032; A61B 6/504; A61B 6/5217; G16H 50/30
See application file for complete search history.

(56) References Cited

U.S. PATENT DOCUMENTS

2017/0265832 A1* 9/2017 Antoniades ............ A61B 6/504

FOREIGN PATENT DOCUMENTS

WO 2018078395 A1 5/2018

OTHER PUBLICATIONS

Antonopoulos et al., "Detecting human coronary inflammation by imaging perivascular fat", Science Translational Medicine, Jul. 12, 2017: vol. 9, Issue 398, eaal2658, doi: 10.1126/scitranslmed. aal2658, pp. 1-12.
(Continued)

*Primary Examiner* — Manuchehr Rahmjoo
(74) *Attorney, Agent, or Firm* — Bookoff McAndrews, PLLC

(57) ABSTRACT

Systems and methods are disclosed for assessing cardiovascular disease and treatment effectiveness based on adipose tissue. One method includes identifying a vascular bed of interest in a patient's vasculature; receiving a medical image of the patient's identified vascular bed of interest; identifying adipose tissue in the received medical image; receiving a geometric vascular model comprising a representation of the patient's identified vascular bed of interest; and computing an inflammation index associated with the geometric vascular model, using the identified adipose tissue.

15 Claims, 4 Drawing Sheets

Related U.S. Application Data

(60) Provisional application No. 62/746,972, filed on Oct. 17, 2018.

(51) Int. Cl.
*G16H 30/20* (2018.01)
*A61B 5/02* (2006.01)
*A61B 5/00* (2006.01)

(52) U.S. Cl.
CPC ........... *A61B 5/7278* (2013.01); *G16H 30/20* (2018.01); *G16H 50/50* (2018.01)

(56) References Cited

OTHER PUBLICATIONS

Antonopoulos et al., "Supplementary Materials for Detecting human coronary inflammation by imaging perivascular fat", Science Translational Medicine, Jul. 12, 2017, vol. 9, Issue 398, eaal2658 (2017) DOI: 10.1126/scitranslmed.aal2658, pp. 1-33.

J Am Coll Cardiol. Apr. 2, 2013;61(13):1388-95. doi: 10.1016/j.jacc.2012.11.062. Epub Feb. 20, 2013. Association of epicardial fat with cardiovascular risk factors and incident myocardial infarction in the general population: the Heinz Nixdorf Recall Study. Mahabadi AA1, Berg MH, Lehmann N, Kälsch H, Bauer M, Kara K, Dragano N, Moebus S, Jöckel KH, Erbel R, Möhlenkamp S.

J Nucl Cardiol. Apr. 2015;22(2):325-33. doi: 10.1007/s12350-014-0004-4. Epub Oct. 24, 2014. Increased regional epicardial fat volume associated with reversible myocardial ischemia in patients with suspected coronary artery disease. Khawaja T1, Greer C, Thadani SR, Kato TS, Bhatia K, Shimbo D, Kontak A, Bokhari S, Einstein AJ, Schulze PC.

\* cited by examiner

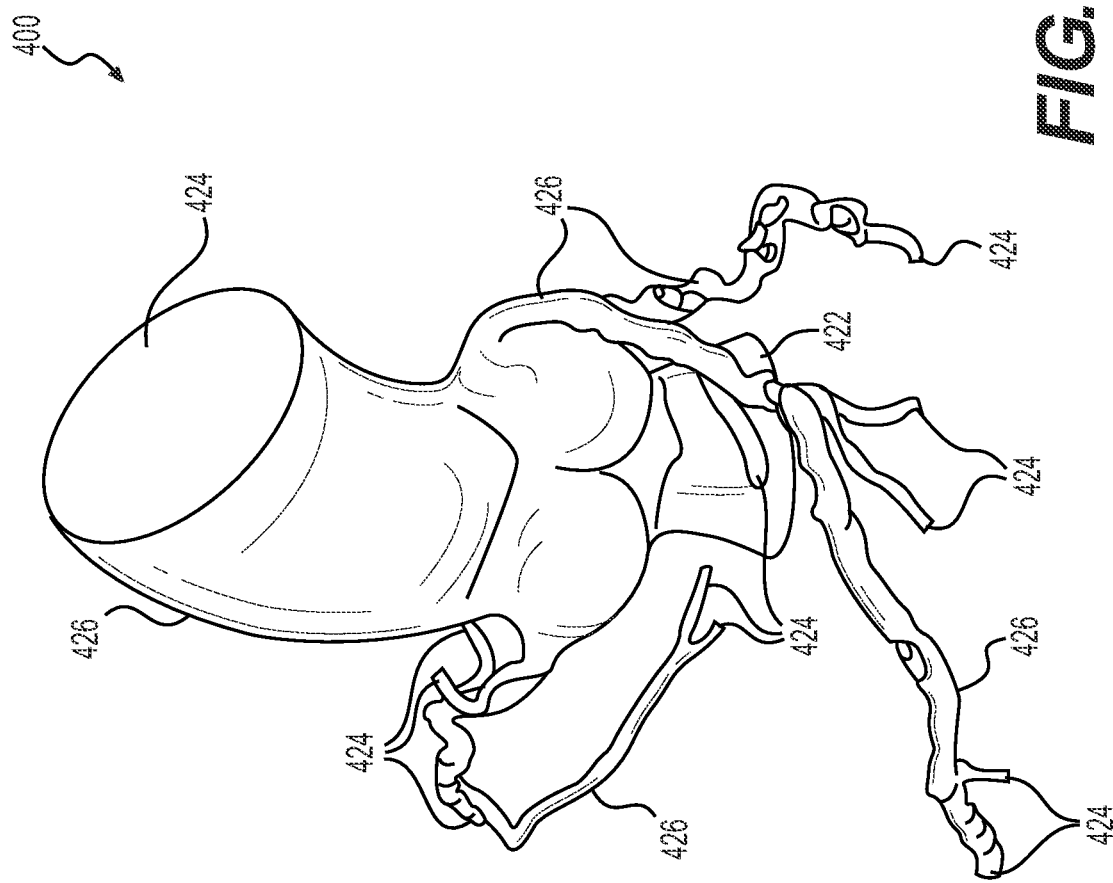

SYSTEM AND METHOD FOR ASSESSING CARDIOVASCULAR DISEASE AND TREATMENT EFFECTIVENESS FROM ADIPOSE TISSUE

RELATED APPLICATION

This application is a continuation of and claims the benefit of priority to U.S. patent application Ser. No. 16/654,698, filed Oct. 16, 2019, which claims priority to U.S. Provisional Application No. 62/746,972, filed Oct. 17, 2018, each of which is incorporated herein by reference in its entirety.

TECHNICAL FIELD

Various embodiments of the present disclosure relate generally to cardiovascular disease assessments and related methods. More specifically, particular embodiments of the present disclosure relate to systems and methods for assessing cardiovascular disease and treatment effectiveness from adipose tissue.

INTRODUCTION

Cardiovascular disease is the leading cause of death worldwide. When a patient has vascular disease, an understanding of the severity of the disease and the responsiveness of that disease to various treatments may be developed. Diagnostic metrics, such as Fractional Flow Reserve (FFR), can be calculated from a Computed Tomography image (FFRct). These diagnostic metrics may provide functional information that can be used to assess the severity of a lesion. Despite advances in technology for vascular disease assessment and treatment, some gaps remain. For example, FFRct calculated from a CT image may not match the FFR measured invasively from a patient. Further, different patients' disease may progress at different rates (sometimes leading to plaque rupture). Patients may also respond differently to medical and invasive therapy.

One area of recent study has focused on understanding the relationship between epicardial adipose tissue (EAT) and various clinical variables. Accordingly, a desire exists to fill existing gaps in cardiovascular disease assessment and treatment, using knowledge of adipose tissue.

SUMMARY

According to certain aspects of the present disclosure, systems and methods are disclosed for assessing cardiovascular disease and treatment effectiveness based on adipose tissue. One method of assessing cardiovascular disease and treatment effectiveness based on adipose tissue includes: identifying a vascular bed of interest in a patient's vasculature; receiving a medical image of the patient's identified vascular bed of interest; identifying adipose tissue in the received medical image; receiving a geometric vascular model comprising a representation of the patient's identified vascular bed of interest; and computing an inflammation index associated with the geometric vascular model, using the identified adipose tissue.

According to another embodiment, a system is disclosed for assessing cardiovascular disease and treatment effectiveness based on adipose tissue. The system includes a data storage device storing instructions for assessing cardiovascular disease and treatment effectiveness based on adipose tissue; and a processor configured to execute the instructions to perform a method including the steps of: identifying a vascular bed of interest in a patient's vasculature; receiving a medical image of the patient's identified vascular bed of interest; identifying adipose tissue in the received medical image; receiving a geometric vascular model comprising a representation of the patient's identified vascular bed of interest; and computing an inflammation index associated with the geometric vascular model, using the identified adipose tissue.

In accordance with yet another embodiment, a non-transitory computer readable medium for use on a computer system containing computer-executable programming instructions for performing a method of assessing cardiovascular disease and treatment effectiveness based on adipose tissue. The method includes: identifying a vascular bed of interest in a patient's vasculature; receiving a medical image of the patient's identified vascular bed of interest; identifying adipose tissue in the received medical image; receiving a geometric vascular model comprising a representation of the patient's identified vascular bed of interest; and computing an inflammation index associated with the geometric vascular model, using the identified adipose tissue.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 4 depicts an exemplary vascular model providing the basis for a blood flow model's boundary conditions, according to an embodiment of the present disclosure.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts. As used herein, the term "exemplary" is used in the sense of "example," rather than "ideal."

Cardiovascular disease is the leading cause of death worldwide. Diagnostic metrics for cardiovascular disease (e.g., FFRct) may be calculated from a CT image, e.g., a computed tomography angiography (CTA) image. Patient images (e.g., CTAs) may also reveal substantial information about the patient's disease, including the degree of stenosis, the plaque composition associated with that stenosis and the amount and composition of adipose tissue present in the local vascular bed. The present disclosure aims to leverage information about a patient's adipose tissue, to improve cardiovascular disease assessment and treatment. The present embodiments describe systems and methods for using information about a patient's adipose tissue to improve blood flow metric accuracy (e.g., FFRct calculation accuracy), so that calculated FFRct may better match invasively obtained FFR. The present embodiments also include systems and methods for using information about a patient's adipose tissue to better predict patient disease progression and response to therapy.

In particular, the present system and methods describe computing a patient-specific inflammation index that may serve as a representation of the patient's adipose tissue volume, location, composition, and relationship to other clinical variables. Each patient's inflammation index may help to assess the patient's disease, predict the patient's responsiveness to treatment(s), and improve accuracy of FFRct computations for the patient.

Figure 1:
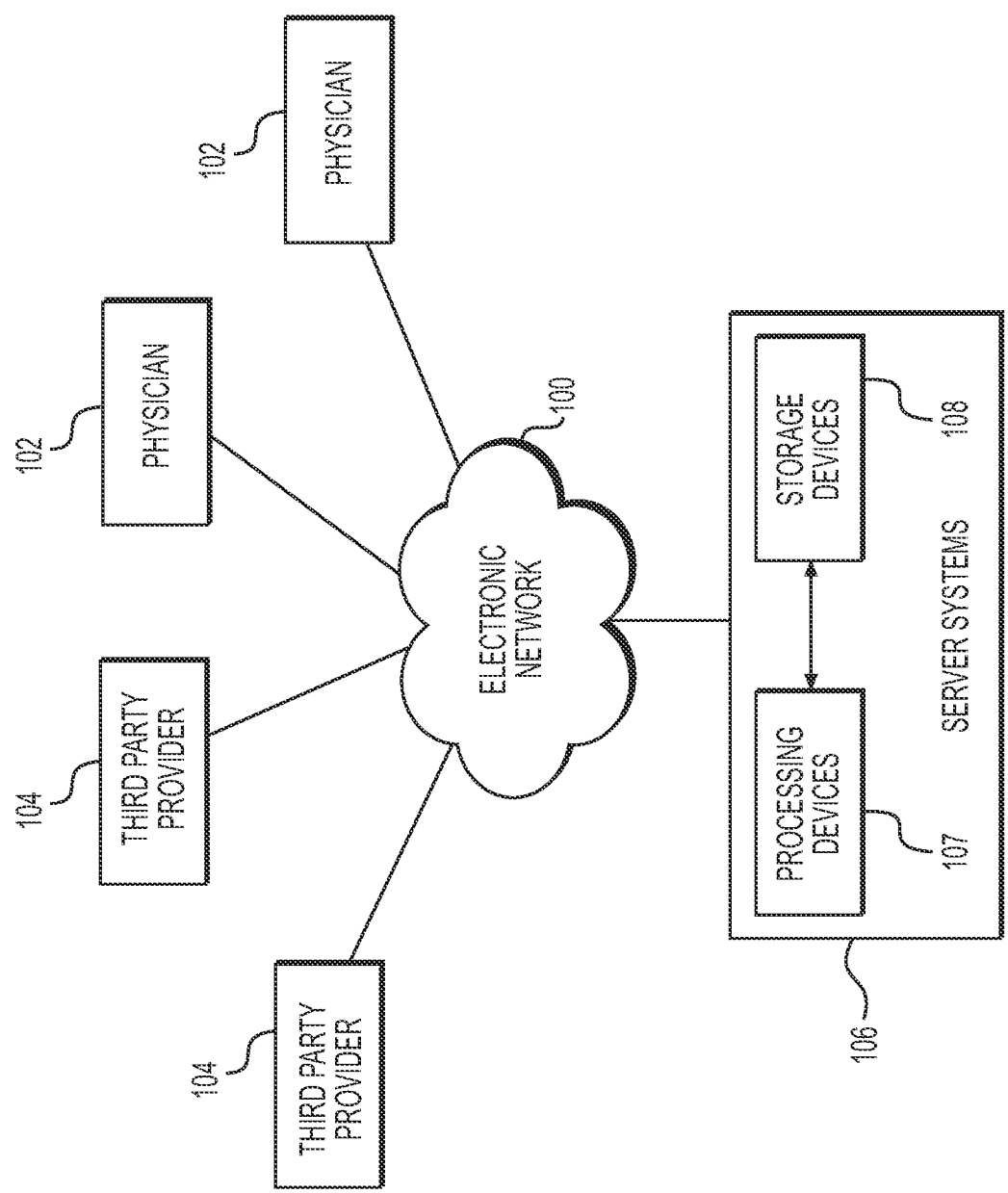
FIG. 1 is a block diagram of an exemplary system and network for assessing cardiovascular disease and treatment effectiveness based on adipose tissue, according to an embodiment of the present disclosure.

Referring now to the figures, FIG. 1 depicts a block diagram of an exemplary system and network for assessing cardiovascular disease and treatment effectiveness based on adipose tissue. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100. Server systems 106 may include storage devices for storing images and data received from physicians 102 and/or third party providers 104. Sever systems 106 may also include processing devices for processing images and data stored in the storage devices. Alternatively or in addition, the present disclosure (or portions of the system and methods of the present disclosure) may be performed on a local processing device (e.g., a laptop), absent an external server or network.

Figure 2:
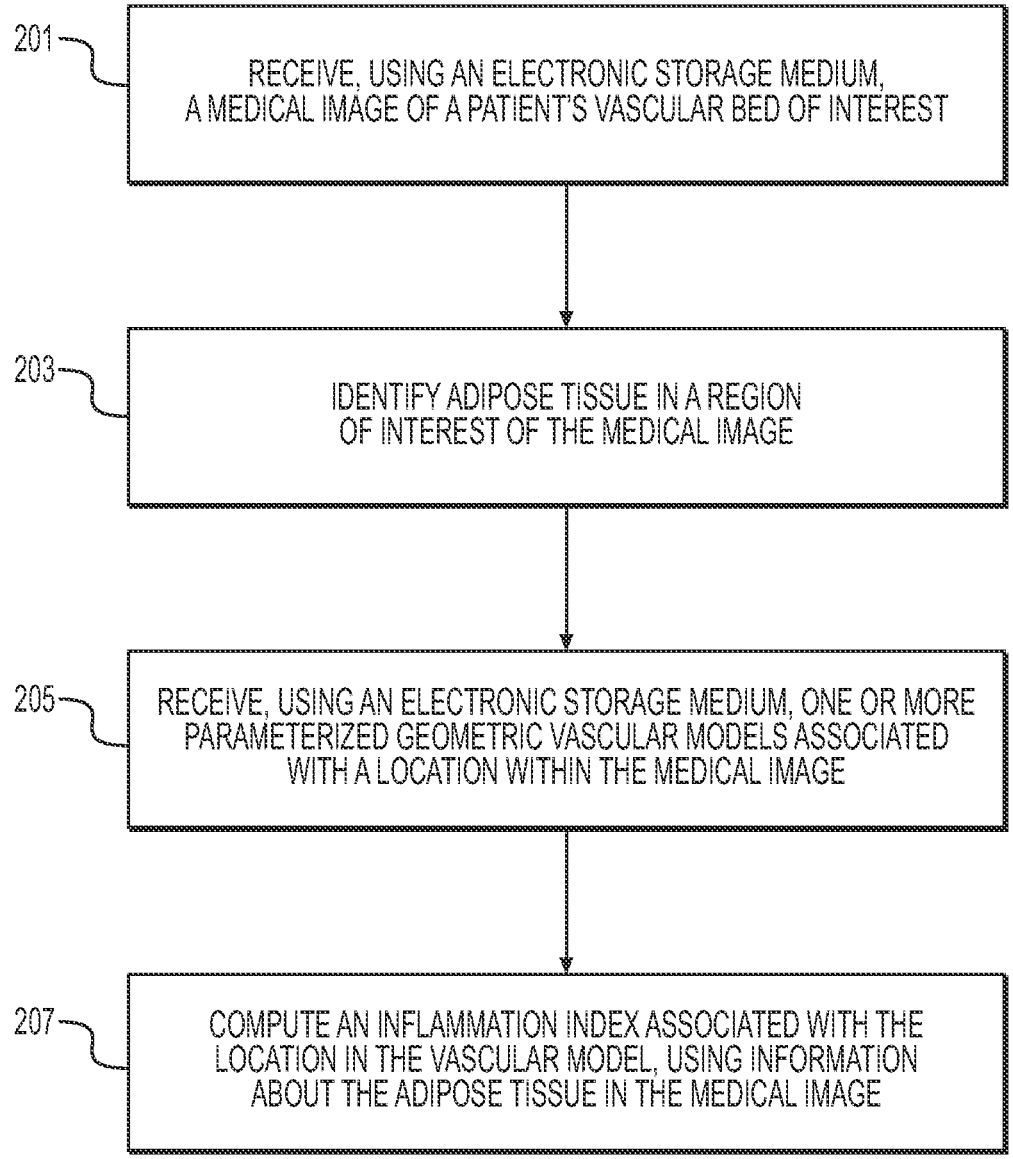
FIG. 2 is an exemplary method for computing a patient's inflammation index, according to an embodiment of the present disclosure.
Figure 3:
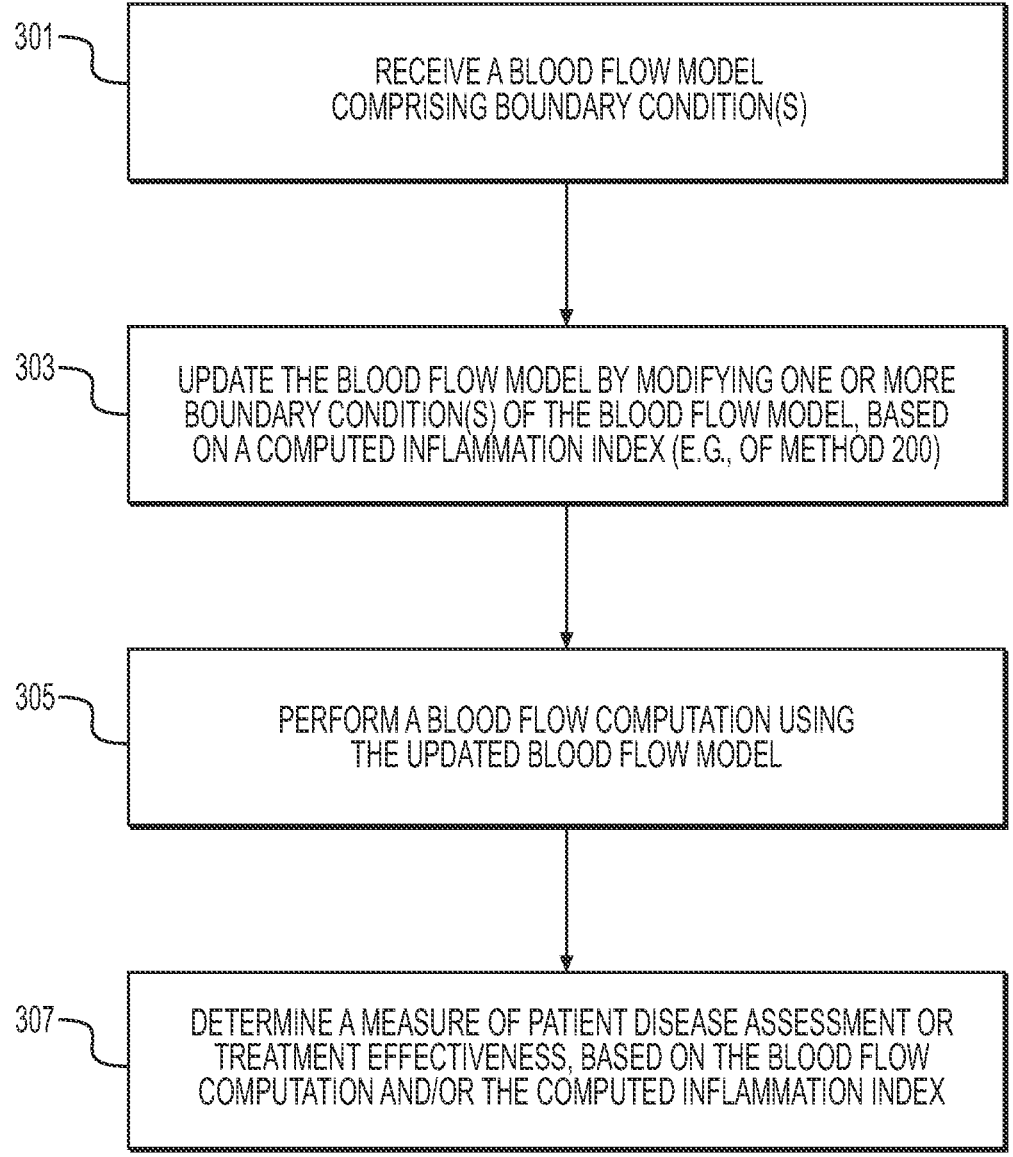
FIG. 3 is an exemplary method for assessing cardiovascular disease and treatment effectiveness based on adipose tissue, according to an embodiment of the present disclosure.

FIGS. 2 and 3 depict flowcharts of computing and applying a patient's inflammation index. In particular, FIG. 2 is a flowchart of an exemplary method 200 of computing an inflammation index for a patient, based on medical image data and a vascular model of the patient's anatomy. FIG. 3 is a flowchart of an exemplary method 300 for using the computed inflammation index to assess the patient's disease or responsiveness to treatment. The methods of FIGS. 2 and 3 may be performed by server systems 106, based on information, images, and data received from physicians 102 and/or third party providers 104 over electronic network 100.

FIG. 2 is a flowchart of an exemplary method 200 for computing an inflammation index, according to an exemplary embodiment of the present disclosure. In one embodiment, step 201 may include receiving, using an electronic storage medium, a medical image of a patient's vascular bed of interest. For example, step 201 may include identifying a patient and a vascular bed of interest in the patient's vasculature. A medical image of the vascular bed of interest may then be received. The received medical image may comprise a coronary computed tomography angiography (CTA) image in one or more cardiac phases and one or more image reconstructions, a non-contrast cardiac computerized tomography (CT) image in one or more cardiac phases and one or more image reconstructions, a dual energy (or multi-energy, spectral) cardiac CT with or without contrast, a cardiac Magnetic Resonance Image (MRI) in one or more cardiac phases and one or more imaging protocols, etc. Similar CT, CTA, or MRI images for other vascular beds, such as the head, neck, thorax, abdomen, pelvis, or legs may also be received as the medical image of the patient's vascular bed of interest.

Exemplary step 203 may include identifying adipose tissue in the received medical image. The identification may be performed via methods, for example, thresholding the received image within a known adipose image intensity range, applying a fat/water separation system to an MRI received image to identify the location of adipose tissue within the MRI, training a machine learning classifier to identify locations of adipose tissue within the received image, etc. Thresholding the image within a known adipose intensity range may include noting adipose tissue within a received medical image based on signal intensities, e.g., in the form of Hounsfield Units (HU). In some forms of imaging, adipose tissue may be represented by negative HU density values, while non-adipose tissue structures may be in a positive HU range. Prompting a display threshold of negative ranges, e.g., −190 and −30 HU may show an estimate of adipose tissue in a CT scan slice, in an exemplary embodiment of step 203.

Alternately or in addition, identifying adipose tissue for step 203 may include applying a separation system to the received image. The separation system may comprise a fat/water separation system e.g., a fat fraction map. An exemplary fat fraction may include a proton-density fat fraction map based on MR signal intensity factors, e.g., a density of hydrogen protons from fat, proton signals associated with mobile fat, hydrogen proton density from various proton species, etc. Other forms of adipose tissue segmentation may employ automated or semi-automated algorithms and machine learning techniques to detect adipose tissue within the received image. Bias field correction, clustering, thresholding, classification, edge detection, and masking steps/algorithms may be used in automated adipose tissue segmentation that may employ machine learning.

In one embodiment, step 203 may include identifying adipose tissue in a region of interest (ROI) of the received medical image. The region of interest may include the entire received medical image. In some cases, the entire medical image may be set as the default ROI if no specific ROI is input by a user or other default setting. Another exemplary ROI may include the vascular bed of interest, such as the interior of the endocardium, interior of the pericardium, outer vessel wall, other muscles (e.g., leg muscles, arm muscles, etc.), or other organs (e.g., brain, kidney, liver, bowel, spleen, etc.). Yet another ROI may include an area or subsection of the received medical image identified/input by a user, automated machine learning algorithm, third party software package, default setting, etc. In addition to identifying adipose tissue, step 203 may include identifying and storing a location of adipose tissue in the ROI. For example, step 203 may include associating the received medical image or ROI with a grid or coordinate system, and noting the location of adipose tissue relative to the grid/coordinate system of the received medical image.

Step 205 may include receiving, using an electronic storage medium, a parameterized geometric vascular model associated with a location within the received medical image. The geometric vascular model may comprise a representation of the patient's identified vascular bed of interest. The vascular model may include a vessel model representing any component of the vessel/vascular bed of interest, such as the lumen, internal/external elastic lamina, plaque deposit(s), or the outer wall. One exemplary parameterization may include a vascular model parameterized by vessel centerline location coordinates, where each centerline location is additionally parameterized by a vessel radius. Another exemplary parameterization may include a vascular model parameterized by identifying voxels within the received medical image which is associated with the vessel.

Step 207 may include calculating or computing an inflammation index associated with the geometric vascular model, using the identified adipose tissue. For example, step 207 may include calculating an inflammation index associated with (or corresponding to) one or more locations in the geometric vascular model (or vessel centerline) (e.g., of step 205) using the information about adipose tissue in the received medical image (e.g., of step 203). The inflammation index may account for EAT composition, including accounting for both EAT hypertrophy and EAT inflammation. EAT volume extracted from the CT image can be used to measure EAT hypertrophy, and the image intensity of the EAT can provide information on EAT inflammatory status. In one instance, an inflammation index may be increased based on the extracted EAT volume/hypertrophy, and increased by another factor, based on the EAT inflammatory status. As one exemplary case, a patient may have a large, but relatively un-inflamed volume or a small inflamed volume. In such a scenario, the patient's inflammation index may be increased to reflect the large EAT volume, but not increased by a second factor since the volume is relatively uninflamed. Had the EAT volume also been inflamed, the inflammation index may be increased by a second factor to reflect the inflammation. One of ordinary skill may recognize that other embodiments may include defining the inflammation index such that EAT volume/hypertrophy or EAT inflammatory status may entail reductions in the inflammation index.

Because the distribution of inflammatory tissue can be heterogenous for a patient, a patient's inflammation index could vary depending on the region of interest in a received image, vascular bed of interest, a specified/selected vascular location or vessel in the vascular bed of interest, and area of identified adipose tissue. A patient could have a different inflammation index for different areas and locations of their body.

This inflammation index may be calculated in multiple ways. One method may include receiving a selected vessel in the vascular bed of interest, receiving a defined distance from the vessel, detecting (based on the received medical image) adipose tissue within the defined distance from the vessel, and quantifying the detected adipose tissue.

The received defined distance may comprise a distance from the selected vessel from which adipose tissue may be measured. For example, the defined distance may include a radius from the centerline of the selected vessel, from which adipose may be measured. This defined distance may be defined because adipose tissue may not be directly adjacent to a vessel, or bounded within the confines of a vessel, e.g., by a vessel wall. Rather, epicardial adipose tissue may be between an epicardial surface of the patient's heart and a visceral surface of the patient's pericardium, fully enclosed by the patient's pericardial sac, surrounding coronary arteries, near the patient's heart or in the patient's mediastinum, or a combination thereof. The embodiments herein may refer to epicardial adipose tissue as including any pericardial fat deposits, and can be extended to include paracardial, intrathoracic, mediastinal fat and any other adipose tissue deposits in proximity to adventitial layer or outside the blood vessel. Accordingly, a distance range may be used to define an area within which adipose tissue may be observed as affecting the selected vessel or the vascular bed of interest. The defined distance may characterize the area within which adipose tissue may be observed. The defined distance may be input by a user or automatically provided. The defined distance may vary, depending on the inflammation index desired. For example, an inflammation index for a specific location in the vascular model for evaluating a given treatment may include a short defined distance. An inflammation index for evaluating an entire vascular bed may include a long defined distance, relative to the defined distance for evaluating the given treatment.

Step 207 may include quantifying the amount of adipose tissue within the specified distance. Alternately or in addition, step 207 may include quantifying a weighted amount of adipose tissue within the defined distance, where each adipose location's contribution to the percentage is weighted by its distance to the selected vessel. For example, the adipose tissue could be weighted by a factor of 5 in close proximity to the selected vessel and a factor of 1 at the limits or boundaries of the extracted or identified EAT volume. "Close proximity" may be defined by a pre-set, automatically determined, or user input distance range. The inflammation index may be computed based on the quantified detected adipose tissue.

Another embodiment of step 207 may include quantifying the percentage of voxels within the defined distance that contain adipose tissue and/or quantifying a weighted percentage of voxels within the defined distance that contain adipose tissue, where each voxel's contribution to the percentage of voxels is weighted by the distance to the vessel. For example, step 207 may include determining, from the medical image, a percentage of voxels containing representations of adipose tissue within the defined distance from the vessel. The detected adipose tissue may then be quantified for this step 207, based on the determined percentage of voxels. Step 207 may include computing an inflammation index based on the quantified detected adipose tissue.

Step 207 may also include using the vessel centerline of the selected vessel to calculate a distance from the vessel centerline normal (e.g., perpendicular) to the adipose tissue. Using this vessel normal, a distance-weighted or distance-unweighted percentage or absolute amount of adipose tissue in the normal direction may be computed. For example, step 207 may include detecting or receiving a centerline of the selected vessel and detecting the adipose tissue based on the defined distance being perpendicular to the centerline of the selected vessel. Method 200 may include calculating inflammation indices for one or more vessel locations in the vascular bed of interest. The inflammation indices may be computed using any method for calculating inflammation, using any defined distance.

FIG. 3 is a flowchart of an exemplary method 300 for assessing cardiovascular disease and treatment effectiveness based on adipose tissue, according to an exemplary embodiment of the present disclosure. Method 200 discussed computing inflammation indices as indicators of the adipose tissue in a patient. Method 300 involves improving blood flow computations based on these computed inflammation indices. Method 300 further entails using the improved blood flow computations to assess patient disease and treatment.

In one embodiment, step 301 may include receiving a blood flow model comprising a physics-based computational fluid dynamics model associated specifically with the patient's vascular bed of interest. For example, the blood flow model may be based on the parameterized geometric vascular model (e.g., from step 205). In such a scenario, the blood flow model may be patient-specific, meaning, the blood flow model may be directly associated with the patient's anatomy, e.g., from the geometric vascular model. Each patient may have a distinct blood flow model, since the blood flow model may be dictated by the patient's unique anatomy. Various embodiments of blood flow models are disclosed, for example, in U.S. Pat. No. 8,315,812 issued Nov. 20, 2012, entitled "Method and System for Patient-Specific Modeling of Blood Flow," which is incorporated by reference in its entirety.

The blood flow model of step 301 may include boundary conditions. The boundary conditions may provide information about the blood flow model at its boundaries, e.g., the inflow boundaries 422 (FIG. 4), the outflow boundaries 424 (FIG. 4), the vessel wall boundaries 426 (FIG. 4), etc. The inflow boundaries 422 may include the boundaries through which flow is directed into the anatomy of the geometric vascular model 400, such as at an end of the aorta near the aortic root. Each inflow boundary 422 may be assigned, e.g., with a prescribed value or field for velocity, flow rate, pressure, or other characteristic, by coupling a heart model and/or a lumped parameter model to the boundary, etc. The outflow boundaries 424 may include the boundaries through which flow is directed outward from the anatomy of the three-dimensional model, such as at an end of the aorta near the aortic arch and the downstream ends of the main coronary arteries and the branches that extend therefrom. Each outflow boundary can be assigned, e.g., by coupling a lumped parameter or distributed (e.g., a one-dimensional wave propagation) model. The prescribed values for the inflow and/or outflow boundary conditions may be determined by noninvasively measuring physiologic characteristics of the patient, such as, but not limited to, cardiac output (the volume of blood flow from the heart), blood pressure, myocardial mass, etc. The vessel wall boundaries may include the physical boundaries of the aorta, the main coronary arteries, and/or other coronary arteries or vessels of the geometric vascular model 400.

Step 303 may include modifying a blood flow computation based on a computed inflammation index (e.g., of step 207). In one embodiment, one or more boundary conditions of the blood flow model may be modified to reflect a decreased microvascular response during hyperemia. For step 303 then, a boundary condition of microvascular resistance may be decreased based on the average (median, maximum) inflammation index in a vessel, to represent dilation from chemically-induced hyperemia or exercise. The microvascular resistance may also be increased based on an inflammation index to represent a narrowing, blockage, or stenosis in a vessel.

The blood flow model having boundary condition(s) modified based on the patient's inflammation index may be used to compute blood flow metrics, e.g., fractional flow reserve (including FFRct). Alternately or in addition, step 303 may include using the modified boundary conditions to recompute blood flow metrics, e.g., FFRct values. The recomputed blood flow metrics may be evaluated to determine whether inclusion of inflammation indices improves diagnostic accuracy. For example, recomputed FFR may be compared to invasively measured FFR. If the FFR recomputed with using boundary condition(s) modified based on the patient's inflammation index more closely matches FFR computed without boundary conditions modified based on the inflammation index, one conclusion may be made that inflammation indices may be used to improve the accuracy of noninvasive FFR computations. Such evaluations may be made for blood flow metrics other than FFR, to determine whether inflammation indices may improve noninvasive, simulated, or predicted computations of the blood flow metrics, e.g., vessel wall shear stress, axial forces, blood pressure, blood pressure gradients, transluminal attenuation gradient, plaque rupture risk, risk of embolism, etc. Machine learning methods may be used to adjust inflammation index parameters in physiologic boundary conditions. For example, machine learning techniques may be used to optimize expected accuracy of computed blood flow metrics against measured blood flow metrics, e.g., computed FFR against (invasively) measured FFR data.

Step 305 may include performing a blood flow computation, based on the computed inflammation index. For example, step 305 may include performing the modified blood flow computation of step 303. Step 307 may include multiple ways of using inflammation indices to assess a patient's cardiovascular disease and response to treatment. For example, step 307 may include determining a measure of patient disease assessment or treatment effectiveness, based on an inflammation index (e.g., computed from method 200). Step 307 may also include outputting the determined measure of patient disease assessment or treatment effectiveness to a display or an electronic storage device. The electronic storage device may be accessed by, for example, by one or more of the parties of FIG. 1, including server systems 106, third party provider(s) 104, and/or physicians 102. Some instances of step 307 or uses of the computed inflammation index for assessing patient disease or treatment are included below. Any of these steps may be used in conjunction with the exemplary steps of method 200.

In one embodiment, methods 200 and/or 300 may include modifying the boundary conditions of a blood flow model to reflect a decreased microvascular response during hyperemia. Specifically, the average (median, maximum) inflammation index in a vessel could be used to increase or decrease a boundary condition comprising a value of microvascular resistance in a selected vessel, to reflect dilation from chemically-induced hyperemia or exercise. For example, a type, volume, or composition of adipose tissue may be associated with vessel(s) vasoconstricting under resting conditions or not vasodilating with increased blood flow. Larger vessels may vasoconstrict under resting conditions from adipose tissue. In response, microvascular resistance may lower to compensate for the large vessels' constriction. During hyperemia or exercise then, microvascular resistance may decrease less (from a resting state microvascular resistance to a hyperemic/exercise state) than in non-inflamed or low adipose tissue areas/patients, since the microvascular resistance is already lower than microvascular resistance in a typical or healthy patient's resting state. Since the computed inflammation index reflects the patient's adipose tissue, the microvascular resistance in a selected vessel may be adjusted to correspond to the vessel's contractile function based on the patient's computed inflammation index. A blood flow computation may then be performed using the blood flow model with the modified boundary conditions. In some embodiments, the blood flow computation may comprise an FFRct calculation. In this case, the measure of disease assessment would be the modified, resultant FFRct score.

In another embodiment, the step 307 may include modifying an interpretation or threshold of a diagnostic blood flow metric, based on the computed inflammation index. Because epicardial adipose tissue (indicated, quantified, or measured by the inflammation index) may be linked to coronary artery disease, a patient's computed inflammation index may affect how their other diagnostic blood flow metrics are interpreted.

For example, for the diagnostic blood flow metric of FFRct, an FFRct score lower than 0.75 or 0.8 is commonly considered to be an indicator of ischemia in a patient, where the ischemia is at a severity level at which invasive or interventional measures may be recommended. The invasive measures may include angioplasty or stenting. FFRct scores higher than 0.8 may be regarded as indicating a healthy patient, or at least a vessel blockage that is not severe enough to warrant invasive intervention. In some embodiments of step 307, the computed inflammation index may be used to "calibrate" conventional blood flow metric thresholds. For example, if 0.8 is a commonly used FFRct threshold value, one scenario may involve adjusting an FFRct threshold score to 0.83, in light of a patient's computed inflammation index.

In other words, for this particular patient, an FFRct score of 0.83 (or lower) may prompt a recommendation for invasive treatment, in contrast to current uses of FFRct, in which invasive treatment may only be suggested for patients with FFRct scores of 0.8 or lower. One particular embodiment may include determining a threshold inflammation index, e.g., based on inflammation indices calculated for a population of users/patients, where the threshold inflammation index may represent an objective division between "high" inflammation indices versus "low" inflammation indices. The high inflammation indices may indicate quantities or locations of adipose tissue where a patient's epicardial adipose tissue is increasing their development of coronary artery disease, whereas low inflammation indices may indicate where a patient's epicardial adipose tissue is not negatively affecting their coronary health. In this embodiment, if a user's computed inflammation index exceeds the determined threshold inflammation index, their FFRct threshold score may also be adjusted from the conventional threshold of 0.8. For example, the adjusted FFRct threshold score may be 0.83 (rather than 0.8) if the patient's inflammation index exceeds the threshold inflammation index.

In some cases, the diagnostic metric adjustment could entail adding or subtracting a function of the inflammation index to the diagnostic metric (e.g., a calculated FFRct in the vessel in which the inflammation index is determined). In this case of step 307, the measure for a patient's disease assessment may comprise the patient's blood flow metric (e.g., computed FFRct) relative to the modified diagnostic metric threshold score (e.g., an adjusted FFRct threshold).

Another embodiment of step 307 may include using machine learning to understand how inflammation indices in a vessel correspond to heart disease. For example, step 307 may include using machine learning and computed inflammation indices in a vessel to predict the local progression or regression of plaque in a selected vessel of the patient. One approach for training the machine learning technique may include predicting that plaque progresses if the local inflammation index is above a first inflammation index threshold, and that the plaque regresses if the local inflammation index is below a second inflammation index threshold. The first inflammation index threshold and the second inflammation index threshold may be preset, input by a user, learned from machine learning processes, validated by population data, or a combination thereof. In this case, an exemplary output indicating a measure of treatment effectiveness may include the prediction of plaque progression/regression if the patient is untreated.

Yet another embodiment of step 307 may include using the inflammation index to assess the likelihood of plaque rupture (plaque vulnerability). This assessment could be performed by using machine learning on the inflammation index local to a plaque to predict rupture. Alternately or in addition, this assessment may include computing or calculating plaque stress (axial, wall shear, etc.) compared to plaque wall strength. In such a scenario, the plaque wall strength may be treated computationally as reduced, where a patient has a high inflammation index. As previously described, a "high inflammation index" may be where a patient's computed inflammation index exceeds a predetermined "high" inflammation index threshold. In some cases, the plaque wall strength may be reduced a by preset amount when the high inflammation index is identified. In other computations, the plaque wall strength may be reduced by an amount corresponding to the extent to which the patient's inflammation index exceeds the high inflammation index threshold.

In short, step 307 may encompass generating a patient disease assessment or treatment evaluation based on the computed inflammation index. The precise use of the inflammation index, patient disease assessment, or treatment evaluation may take many forms, including the ones detailed above.

In summary, a patient's epicardial adipose tissue may impact their risk of cardiovascular disease. The epicardial adipose tissue may also influence the patient's responsiveness to treatment. The disclosed systems and methods improve upon past cardiovascular disease assessments and treatments by accounting for the effects of epicardial adipose tissue in the patient. In particular, the disclosed embodiments describe computing an inflammation index for each patient, to represent the epicardial adipose tissue of the patient. The disclosure further describes ways to use the computed inflammation index to improve cardiovascular diagnostics, predictions, and treatment recommendations.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for assessing cardiovascular disease and treatment effectiveness based on adipose tissue, the method comprising:
   identifying a vascular bed of interest in a patient's vasculature;
   receiving a medical image of the patient's identified vascular bed of interest;
   receiving a selected vessel in the vascular bed of interest;
   receiving a defined distance from the vessel, the defined distance being a distance from the selected vessel from which adipose tissue may be measured;

detecting a centerline of the selected vessel;
detecting, based on the medical image and on the defined distance being perpendicular to the centerline of the selected vessel, adipose tissue within the defined distance from the vessel;
identifying the adipose tissue in the received medical image;
receiving a geometric vascular model comprising a representation of the patient's identified vascular bed of interest;
computing an inflammation index associated with the geometric vascular model, using the identified adipose tissue; and
quantifying the detected adipose tissue.

2. The method of claim 1, further comprising:
computing the inflammation index based on the quantified detected adipose tissue.

3. The method of claim 1, further comprising:
determining, from the medical image, a percentage of voxels containing representations of adipose tissue within the defined distance from the vessel; and
quantifying the detected adipose tissue based on the determined percentage of voxels.

4. The method of claim 3, further comprising:
computing the inflammation index based on the quantified detected adipose tissue.

5. The method of claim 1, further comprising:
modifying a blood flow computation based on the computed inflammation index.

6. The method of claim 1, further comprising:
generating a patient disease assessment or treatment evaluation based on the computed inflammation index.

7. A system for assessing cardiovascular disease and treatment effectiveness based on adipose tissue, the system comprising:
a data storage device storing instructions for assessing cardiovascular disease and treatment effectiveness based on adipose tissue; and
a processor configured to execute the instructions to perform a method including:
identifying a vascular bed of interest in a patient's vasculature;
receiving a medical image of the patient's identified vascular bed of interest;
receiving a selected vessel in the vascular bed of interest;
receiving a defined distance from the vessel, the defined distance being a distance from the selected vessel from which adipose tissue may be measured;
detecting a centerline of the selected vessel;
detecting, based on the medical image and on the defined distance being perpendicular to the centerline of the selected vessel, adipose tissue within the defined distance from the vessel;
identifying the adipose tissue in the received medical image;
receiving a geometric vascular model comprising a representation of the patient's identified vascular bed of interest;
computing an inflammation index associated with the geometric vascular model, using the identified adipose tissue; and
quantifying the detected adipose tissue.

8. The system of claim 7, wherein the system is further configured for:
computing the inflammation index based on the quantified detected adipose tissue.

9. The system of claim 7, wherein the system is further configured for:
determining, from the medical image, a percentage of voxels containing representations of adipose tissue within the defined distance from the vessel; and
quantifying the detected adipose tissue based on the determined percentage of voxels.

10. The system of claim 9, wherein the system is further configured for:
computing the inflammation index based on the quantified detected adipose tissue.

11. The system of claim 7, wherein the system is further configured for:
modifying a blood flow computation based on the computed inflammation index.

12. The system of claim 7, wherein the system is further configured for:
generating a patient disease assessment or treatment evaluation based on the computed inflammation index.

13. A non-transitory computer readable medium for use on a computer system containing computer-executable programming instructions for performing a method of assessing cardiovascular disease and treatment effectiveness based on adipose tissue, the method comprising:
identifying a vascular bed of interest in a patient's vasculature;
receiving a medical image of the patient's identified vascular bed of interest;
receiving a selected vessel in the vascular bed of interest;
receiving a defined distance from the vessel, the defined distance being a distance from the selected vessel from which adipose tissue may be measured;
detecting a centerline of the selected vessel;
detecting, based on the medical image and on the defined distance being perpendicular to the centerline of the selected vessel, adipose tissue within the defined distance from the vessel:
identifying the adipose tissue in the received medical image;
receiving a geometric vascular model comprising a representation of the patient's identified vascular bed of interest;
computing an inflammation index associated with the geometric vascular model, using the identified adipose tissue; and
quantifying the detected adipose tissue.

14. The non-transitory computer readable medium of claim 13, the method further comprising:
computing the inflammation index based on the quantified detected adipose tissue.

15. The non-transitory computer readable medium of claim 13, the method further comprising:
determining, from the medical image, a percentage of voxels containing representations of adipose tissue within the defined distance from the vessel; and
quantifying the detected adipose tissue based on the determined percentage of voxels.

* * * * *